(12) United States Patent
Guedon et al.

(10) Patent No.: US 7,678,584 B2
(45) Date of Patent: Mar. 16, 2010

(54) METHOD FOR CHARACTERIZING A SURFACE, AND DEVICE THEREFOR

(75) Inventors: Philippe Guedon, Arcueil (FR); Yves Levy, Malakoff (FR)

(73) Assignee: Institut d'Optique Theorique et Appliquee, Orsay (FR)

( * ) Notice: Subject to any disclaimer, the term of this patent is extended or adjusted under 35 U.S.C. 154(b) by 524 days.

(21) Appl. No.: 11/592,221

(22) Filed: Nov. 3, 2006

(65) Prior Publication Data

US 2007/0054392 A1 Mar. 8, 2007

Related U.S. Application Data (62) Division of application No. 10/450,401, filed as application No. PCT/FR01/03991 on Dec. 13, 2001, now abandoned.

(30) Foreign Application Priority Data

| Dec. 13, 2000 | (FR) | ................................. 00 16247 |
| Dec. 13, 2000 | (FR) | ................................. 00 16248 |

(51) Int. Cl.
*G01N 33/552* (2006.01)
(52) U.S. Cl. ............... 436/527; 436/518; 436/524; 436/525; 435/283.1; 435/287.1; 435/288.7
(58) Field of Classification Search ............... None
See application file for complete search history.

(56) References Cited

U.S. PATENT DOCUMENTS

| 4,521,522 A | 6/1985 | Lundstrom et al. |
| 5,017,009 A | 5/1991 | Schutt et al. |
| 5,220,397 A | 6/1993 | Huang et al. |
| 5,341,215 A | 8/1994 | Seher |
| 5,434,663 A | 7/1995 | Maule |
| 5,455,178 A | 10/1995 | Fattinger |
| 5,965,456 A | 10/1999 | Malmqvist et al. |
| 5,999,262 A | 12/1999 | Dobschal et al. |
| 6,025,139 A | 2/2000 | Yager et al. |
| 6,218,194 B1 | 4/2001 | Lyndin et al. |
| 6,493,097 B1 | 12/2002 | Ivarsson |
| 6,579,726 B1 | 6/2003 | Natan et al. |
| 6,731,388 B1 | 5/2004 | Simon et al. |

FOREIGN PATENT DOCUMENTS

| JP | A-09-292335 | 11/1997 |
| WO | WO 98/34098 | 8/1998 |
| WO | WO 00/70328 | 11/2000 |
| WO | WO 01/35081 A1 | 5/2001 |

OTHER PUBLICATIONS

Lyon L. Andrew et al., "An Improved Surface Plasmon Resonance Imaging Apparatus," Review of Scientific Instruments, vol. 70, No. 4, Apr. 1999, pp. 2076-2081, XP000875403, American Institute of Physics.

*Primary Examiner*—Melanie J. Yu
(74) *Attorney, Agent, or Firm*—Oliff & Berridge, PLC (57) ABSTRACT

The present invention relates to a method of characterizing a surface and to a device for implementing this method. In particular, this method makes it possible to measure, qualitatively and/or quantitatively, interactions that may be physical, chemical, biochemical or biological.

11 Claims, 2 Drawing Sheets

FIG.1

METHOD FOR CHARACTERIZING A SURFACE, AND DEVICE THEREFOR

This is a Divisional of application Ser. No. 10/450,401, which is a National Phase of Application No. PCT/FR01/03991 filed Dec. 13, 2001. The entire disclosures of the prior applications are hereby incorporated by reference in their entirety.

The present invention relates to a method of characterizing a surface and to a device for implementing this method. In particular, this method makes it possible to measure, qualitatively and/or quantitatively, interactions that may be physical, chemical, biochemical or biological.

Most existing methods in this field use fluorescent markers to reveal the molecular interactions and need to work under specific conditions. These specific conditions do not allow several types of interaction to be analyzed simultaneously. In contrast, the method of the invention makes it possible in particular to follow, in real time, and without markers, up to several hundred molecular interactions both qualitatively and quantitatively.

The method of the invention allows characterization of the surface of a sensitive film, deposited on the base of an optical prism, using a technique based on the analysis of the variation in the reflectivity of the prism/sensitive film interface. This reflectivity is likely to vary with the angle of incidence of a light beam directed into the prism toward one part of the interface corresponding to a part of said surface to be characterized. This reflectivity also varies with the optical thickness of the sensitive film so that the method of the invention makes it possible in particular to characterize the change in zones of the sensitive film, the optical thickness of which is likely to vary with time. That part of the interface "corresponding" to the part to be characterized is, of course, that part facing the part of the surface to be characterized.

The method of the invention can be used in particular either in techniques based on surface plasmon resonance or in techniques based on interferometry and using the coupling between a prism and a waveguide.

The subject of the invention is in particular a method of characterizing the surface of a sensitive film, said surface having active zones whose optical thickness is likely to vary with time, said sensitive film being deposited on the base of an optical prism, said method using a technique based on analyzing the variation in the reflectivity of the prism/sensitive film interface, in which:

a) a collimated light beam is made to enter the prism, via an entrance face, at an angle of incidence allowing total reflection on the base of the prism, said beam illuminating a fixed part of the interface corresponding to a part to be characterized, called useful part, of said surface, and the reflected beam emerging as the emergent beam via the exit surface of the prism;

b) an angular scan of the useful part is carried out by varying the angle of incidence of said beam so as to record an angle of incidence for which the reflectivity of at least part, or of all, of the active zones is a minimum;

c) an optimum angle of incidence, for which the sensitivity of detecting the active zones is a maximum, is determined;

d) the angle of incidence is set to the optimum value determined in the previous step; and the reflectivity is measured using an imaging/detection system having a sensitive surface capable of receiving the entire emergent beam emanating from the useful part.

A collimated beam is a beam in which all the rays are parallel.

The prism is used in the method and the device of the invention as a coupling prism, using the phenomenon of total reflection on an interface.

The surface to be characterized of the sensitive film is that of the external face of the sensitive film, in contact with the outside medium.

In practice, the thin sensitive film may be deposited either on the base of the prism or on a flat transparent plate with parallel faces, having the same index or an index similar to that of the prism, and fixed, or capable of being fixed, to the base of the prism, with the sensitive film deposited on the external face, which is not in contact with the base of the prism. When this external face is fixed to the prism, this face may be regarded as the true base of the prism in such a case.

The sensitive film may be a thin metal film, and in this case the method of the invention uses the phenomenon of surface plasmon resonance. Among the metals used, mention may in particular be made of gold and silver. A thin metal interlayer, for example of chromium, may be used to improve the bonding of the gold film to the glass of the prism. It is also possible to deposit a film of silver on the prism, the silver film itself being covered with a gold film, thereby allowing the silver to be protected from oxidation.

The sensitive metal film may be deposited on the base of the prism or on a thin film, deposited on the base of the prism, of a low-index dielectric (with an index equal or close to that of the prism).

The sensitive film may also be a thin transparent film of a high-index dielectric capable of acting as a waveguide. In this case, two thin dielectric layers are deposited on the base of the prism, firstly a thin film (for example of silica) serving as spacer medium, having an intermediate index between that of the prism and that of the guiding film, and then the guiding film, of high index. The guiding film may be made, for example, from stoichiometric or non stoichiometric titanium or osmium oxides. The guiding film may itself be covered with a thin metal film.

When the sensitive film is a film of dielectric serving as waveguide, the method of the invention makes it possible in particular to use the waveguide as a resonant mirror system requiring a coherent light source. The principle and the applications of the resonant mirror are known; see for example R. Cush et al., Biosensors & Bioelectronics 8, 347-353 (1993); P. E. Buckle et al, Biosensors & Bioelectronics 8, 355-363 (1993); S. F. Bier, Sensors & Actuators B, 29, 37-50 (1995); C. Stamm et al, Sensors & Actuators B. 31. 203-207 (1996); A. Bernard et al., Eur. J. Biochem, 230, 416-423 (1995). The contents of these documents from the literature as well as the documents mentioned below, are incorporated into the present description by reference.

The thin films used in implementing the method of the invention may be deposited using known methods, for example by vacuum evaporation, sputtering, CVD, MOCVD, etc.

In the following, reference will usually be made to the surface plasmon resonance phenomenon to simplify the description, but experts will readily understand that the method of the invention can be applied without any difficulty to a device using a resonant mirror system.

As indicated above, the method of the invention can be used in particular by exploiting the known phenomenon of surface plasmon resonance (SPR). This phenomenon is observed when a light beam undergoes a reflection at the glass/metal interface of a thin metal film deposited on the base of the prism. When a ligand for an analyte of interest is fixed to the external face of the metal film, and when the metal film is brought into contact with a medium, whether liquid or gaseous, capable of containing the analyte, the latter, if it is present, will become attached, by affinity, to the ligand and this results in a modification of the thickness of the molecular films fixed to the metal surface, and therefore of the optical thickness, this being manifested, in particular because of the SPR phenomenon, by a variation in the reflectivity of the interface.

The optical phenomenon of surface plasmon resonance was discovered some thirty years ago (E. KRETSCHMANN & H. RAETHER; Z. Natürforsch., 23a (1968), 615-617) and was first used for quantitatively characterizing thin nonorganic films (W. P. CHEN & J. M. CHEN, J. Opt. Soc. Am, 71 (1981), 189-191). The optical principle relies on access to the variation in the optical thickness (the refractive index multiplied by the geometrical thickness) via the measurement of the variation in reflectivity on a metal/dielectric interface caused by the fixing of a material to the external face of a metal film. Since the 1980s, the surface plasmon resonance phenomenon has been used in biological applications, in particular in quantitatively characterizing biological interactions. Thus, it is possible, by knowing the refractive index variation, to obtain the number of biological molecules that have interacted (J. A. DE FEIJTER et al., Biopolymers, 17 (1978), 1759-1772; A. BERNARD et al., Eur. J. Biochem., 230 (1995), 416-423; J. PIEHLER et al., J. of Immunol. Methods, 201 (1997), 189-206; P. GUEDON et al., Anal. Chem., (2000) 6003-6009), their concentration and the rates in real time characterizing the interaction of analytes with ligands immobilized beforehand on a thin metal film.

One benefit of the method and of the device of the invention lies in the fact that it is possible to deposit various ligands locally, in a regular fashion, on the sensitive film, in an ordered system (for example, a matrix or hexagonal pattern) in which each separate deposit of small area, or spot, is spatially identifiable (called "address" ligands).

It is known that the variation in reflectivity due to the SPR phenomenon depends on the angle of incidence of the light beam undergoing the total reflection. The phenomenon of total reflection on an interface occurs when a light wave passing through a medium of refractive index $n_1$ encounters a medium of refractive index $n_1$ encounters a medium of refractive index $n_2$ (where $n_2 < n_1$) with an angle of incidence $\alpha$ such that $\alpha > \alpha_c = \arcsin(n_2/n_1)$. When the thickness of the sensitive film increases (especially when an analyte is fixed to immobilized ligands on the metal film), the intensity of the reflected light decreases, then passes through a minimum and then increases again, this phenomenon being observed for a variation in the angle of incidence of several degrees. It is therefore desirable to record, prior to the contacting with the analyte, the angle of incidence for which the intensity of the reflected light is a minimum on the spots, this being manifested by an appreciable contrast between the spots and the bare zones of the substrate. Knowing the precise value of this angle for each spot allows their surface state to the characterized. As a result, depending on the molecular mass of the analyte or analytes, it is possible to determine an angle that optimizes the detection sensitivity for each spot to which an analyte is fixed (or is fixed in larger quantity).

When the optical thickness of the sensitive film increases, for example when an analyte is fixed to the spots containing immobilized ligands, this causes a shift of the resonance peak (reflectivity minimum) toward decreasing external angles of incidence (the term "external angle of incidence" means here the angle of incidence of the light beam in the external environment before entering the prism). By choosing an external angle of incidence close to, but slightly greater than, the initial angle of incidence of the peak (corresponding to a reflectivity close to the minimum), this shift of the peak will entail, for the angle of incidence thus chosen, an increase in the reflectivity, which will be manifested on the image by the appearance of a brighter area (or by the variation in the gray level toward lighter grays), whereas the spots whose optical appearance has not varied will remain dark. The optimum angle of incidence used in accordance with the method of the invention, for which the detection sensitivity is a maximum for all the spots whose optical thickness is likely to vary, can therefore be easily determined. In fact, in the initial state, these spots most of the time have very close resonance peaks. Furthermore, since the angular scan has made it possible to accurately determine the angle of incidence of the resonance peak for each spot in the initial state, it is possible to determine, for each spot, using computing means, the exact value of the shift of the peak for this spot, and therefore it is possible to normalize the results collecting by the detector of the imaging system that detects the flux of photons emanating from each of these spots.

In particular embodiments, the method of the invention may also have the features, taken individually or, as the case may be, in combination, as defined in the claims.

To be able to characterize the change in the active zones of the useful part, the reflectivity is measured as a function of time, either continuously or at predetermined intervals.

The variation in reflectivity is proportional to the number of molecules that are fixed to the spots, this fixing corresponding to an increase in the thickness on the spot in question.

For example, it is possible to fix, on the useful part of the sensitive film:
- antigens (to search for specific antibodies);
- random peptides, to search for specific mimotypes of a given antibody;
- antitumor antibodies, to search for tumor antigens in ground cell matter; and
- all the specific ligands of particular cells, for cell sorting.

The method of the invention can also be used to study all the interactions between the immobilized molecules and the analytes, including cells.

The method of the invention can also be used for screening small molecules that have been immobilized on the active film (for example olegosaccharides) able to inhibit the signaling or enzymatic role of a protein (the analyte is then the protein). The small molecules are selected by a biological or biochemical affinity for proteins or cells.

The subject of the invention is also an imaging device for implementing the method of the invention. This device can be used in particular for imaging the surface of a sensitive film supporting many organic sensors, that is to say a surface on which one or more populations of ligands have been immobilized. These sensors may be deposited on the sensitive film in the form of spots forming a matrix of addressed ligands. These spots may be formed either by deposits on the surface of the sensitive film, or by the filling of wells produced (for example by laser abrasion) on the surface of the sensitive film.

The device of the invention comprises an imaging device for implementing the method of any one of the preceding claims, comprising:
- an optical prism having an entrance face, an exit face and a base provided with a sensitive film, said prism being characterized by its apex angle and by the refractive index of the material of which it is made;
- a first afocal optical conjugation system which is placed on the same side of the entrance face of the prism and the optical axis of which, fixed with respect to the prism, is oriented so that a collimated incident light beam having passed through it is directed toward said entrance face, is refracted, then strikes the base of the prism where it undergoes total reflection and emerges, after refraction, on the exit face, forming an emergent beam, said first conjugation system having an orientation and an aperture that are such that said incident beam refracted on the entrance face illuminates all of at least what is called a useful part of said sensitive film, and undergoes thereon a total reflection when the direction of the incident beam varies, on either side of said optical axis, over an angular range of at least 10° in total, said useful part containing active zones whose optical thickness is likely to vary over time;

a second afocal optical conjugation system which is placed on the same side as the exit face of the prism and of which the optical axis, fixed with respect to the prism, is oriented so that an incident beam parallel to the optical axis of the first conjugation system gives an emergent beam parallel to the optical axis of the second conjugation system;

a detection system having a plane sensitive surface, which is capable of receiving and analyzing the light that has passed through said second conjugation system and which is perpendicular to the optical axis of the latter;

in which:
(i) said second conjugation system has an aperture such that all of the light emanating from the useful zone passes through it when the direction of the incident beam varies over said angular range and the second conjugation system is such that all of the light emanating from the useful zone illuminates the sensitive surface of the detection system; and
(ii) the apex angle and the index of the prism are such that, when the direction of the incident beam is parallel to the optical axis of the first conjugation system, the intermediate image of the useful part, through the exit face of the prism, which constitutes the object for the second detection system, is perpendicular to the optical axis of the latter.

The angular scan that has to be made in order to be able to observe the resonance at various points in the active zone, and its shift during the change of the system over time, varies depending in particular on the metal, the glass, the wavelength, etc. In general, it is at least about 10°.

To study the reflectivity as a function of the external angle of incidence of a metal/dielectric interface requires an angular scan of generally between 4 and 10 degrees, approximately, depending on the wavelength used and the nature of both the dielectric and the metal. For example, with a glass/metal interface at the base of a prism having an apex angle of 30.6 degrees, an index of 1.776 and a thin gold film 45 nm in thickness, and a light source of 600 nm wavelength, it is necessary to scan over a range of approximately 8 degrees in order to completely describe the resonance of the surface plasmons.

Furthermore, if the thin metal film is provided with a plurality of spots, consisting for example of polymers carrying immobilized biological species, the resonance in the case of gold is broken, over all the parts of the sensitive film supporting a spot, and the resonance is then shifted toward decreasing external angles of incidence. For example, for a spot 3 nm in thickness and having an index of 1.7 at 660 nm, the resonance is shifted by approximately 2 degrees. If the sensitive film is then brought into contact with a fluid containing analytes capable of interacting with the biological species immobilized on the spots, a new shift in the resonance, possibly ranging up to approximately 4 degrees, will be observed.

The sum of the angular excursions to be traveled if it is desired to observe the resonances of the gold, of the spots of polymers carrying biological species, and of some of these spots after they have interacted with the analytes, therefore requires a total angular scan of 14 degrees. It is desirable to be able to use an angular scan of 16 degrees, so as to be able to work with a degree of comfort and be able to modify the aforementioned materials at will, especially in terms of index and thickness. In certain applications and with certain materials and certain wavelengths, the possibility of using an angular scan of 10° may suffice. However, the device of the invention does allow an angular scan of possibly up to 16° to be used.

The light source is a coherent source or an incoherent source. In the case of a waveguide device, it is necessarily coherent.

The collimation system may be any conventional optical system for converting a divergent light beam into a parallel beam.

The optical deflector system comprises, for example, a rotating plane mirror that can be mounted on a stepper motor or a DC motor. It is also possible to use a galvanometer mirror. It is known that, when a rotating mirror rotates through a given angle, the reflected ray resulting from a fixed incident ray is deflected through an angle twice said given angle. The rotating plane mirror may in particular be capable or pivoting about an axis parallel to one edge of the prism. This edge of the prism is the line of intersection of the two planes containing the entrance and exit faces of the prism, respectively.

The device of the invention may include a polarizing system, placed for example between the collimation system and the rotating mirror and allowing the light to be polarized parallel to the edge of the prism. The polarizing system is, for example, composed of a simple polarizer or a polarizing beam splitter cube. In the case of a resonant mirror system, a second polarizer is, of course, needed after the prism.

In particular embodiments, the device of the invention may also have features, taken individually or, as the case may be, in combination, as defined in the claims.

In the present invention, the term "dioptric system" is understood to mean a lens or a doublet.

The device of the invention makes it possible to detect, at the best angle of incidence, the variation in the optical thickness (the geometrical thickness multiplied by the refractive index of the material) on the metal/external medium interface without having to modify the position of the elements of the device, which are all fixed with respect to one another, with the exception of the rotating mirror. It is thus very easy to vary the angle of incidence during a preliminary study, by actuating the single rotating mirror, in order to determine the reflectivity of the sensitive zone for each angle of incidence, and it is then possible to take the actual measurements by immobilizing the rotating mirror in the position corresponding to this predetermined optimum angle of incidence.

According to one particular embodiment, the optical imaging device of the invention is such that the image of the useful zone of the thin metal film occupies a maximum area of the CCD detection matrix so that it is the entire area of the useful zone of the metal film that can be analyzed simultaneously by means of the CCD matrix.

An important feature whereby the detection device can receive all the light rays emanating from the image of the useful area of the thin metal film, although the imaging system and the detection system are stationary with respect to the prism, is that the device of the invention includes an optical conjugation system such that the beam, which, after entering the prism, strikes the thin metal film, illuminates the entire useful area of the CCD matrix, and does so whatever the angle of incidence of said beam over said angular range, possibly of up to at least approximately 16°. Such an optical conjugation system may for example be developed, in a known manner, using a device whose aperture number, that is to say the ratio of the focal length to the useful diameter of the optic, is less than N=1/(2 sin 16°/2))=3.6 in order to accept all the beams reflected by the sensitive zone, over the angular range of at least 16°. The conjugation system may, for example, be formed from a first lens of 80 mm focal length and 31.5 mm diameter and a second lens of 65 mm focal length and 25 mm diameter (the combination having an aperture of 2.6), said lenses being placed in such a way that the image of the useful part via the exit face of the prism is roughly in the object focal plane of the first lens, that the image focal plane of the first lens is coincident with the object focal plane of the second lens and finally the CCD matrix lies in the image focal plane of the second lens; in this way, an afocal conjugating device has been formed. It is also possible, for example, to use a third lens, usually called a "field lens", that allows the beams to be brought back toward the optical axis, thus increasing the aperture of the system compared with a two-lens afocal system (see M. BORN & E. WOLF, Principles of Optics, Chapter VI, Pergamon Press, 1959).

Another important feature of one particular embodiment of the device of the invention, which allows each spot of the useful part to be analyzed with satisfactory sensitivity, is that the apex angle and the index of the prism are chosen so that the intermediate image of the useful zone formed in the prism (that is to say the image of the useful surface through the plane dioptric interface formed by the exit face of the prism, and which constitutes the object for the optical imaging system receiving the emergent beam) delivers, in the optical imaging system, an image coincident with the focal plane of the detection system (CCD matrix), or an image very close to this plane and parallel to the latter, or having, with respect to this plane, an angle of inclination low enough to avoid blurring of the image over the entire area.

It is known that any optical imaging system has a certain depth of field, that is to say a longitudinal range, along the optical axis defined by the detector (this optical axis being perpendicular to the plane of the detector), for which the image on the detector will appear sharp. The depth of field depends directly on the focal length of the optical system and its aperture. Thus, for a given focal length, the depth of field increases with the aperture number (the ratio of the focal length to the diameter of an optic). However, the aperture number must also be as small as possible in order to let the maximum number of rays pass through the system, and thus allow a high angular acceptance. Since these conditions are contradictory, a compromise has to be found.

To obtain a sharp image on the detector, the inclination of the image of the useful zone via the exit face of the prism with respect to a plane perpendicular to the optical axis must be low enough for it not to be outside the depth of field defined by the detection system. However, the inclination of the incident beam in this system requires the image to be rectified by a suitable optical device, which may be carried out either by inclining the optic of the imaging system or by inclining the detection system (CCD camera) so as to have the image of the entire sharp area on the CCD detector.

The problem of the inclination of the optic means that said optic is very open in order to let all the rays through this optic, since the angles involved may be relatively large; for example, for an isosceles prism of 1.515 index and 60° apex angle, this imposes an aperture number of the detection system of 0.55, which is unacceptable since such a system exhibits substantial aberration and has a very small depth of field. Similarly, inclining the camera would result in a loss of sharpness due to the fact that the system would no longer work under correct imaging conditions, as one can then no longer speak of aplanatism.

The novelty of the prism and of the optics that are used in an embodiment of the device of the present application lies in the fact that, whatever the angle of incidence of the beam at the prism/sensitive film interface (within the limits of variation indicated for the angle of incidence on the entrance face of the prism), the inclination of the intermediate image via the exit face of the prism varies little, and remains almost perpendicular to the optical axis of the detection system. Thus, a totally reflected ray coming from the center of the useful zone will make, on exiting the prism, a small angle to the optical axis of the imaging system, whereas the corresponding image point on the detector will remain roughly within the limits of the depth of field defined by this system.

A major benefit of the device of the invention is that all of the optical elements are stationary (apart from the rotating mirror) and the optics are of low aperture (they consequently exhibit less aberration and allow a high depth of field), and to do so without impairing the performance in terms of focussing and angular acceptance, which may especially be up to 16°, of the system.

Other objects and advantages of the invention will become apparent during the following description with reference to the appended drawings given by way of non-limiting example, in which.

Figure 1:
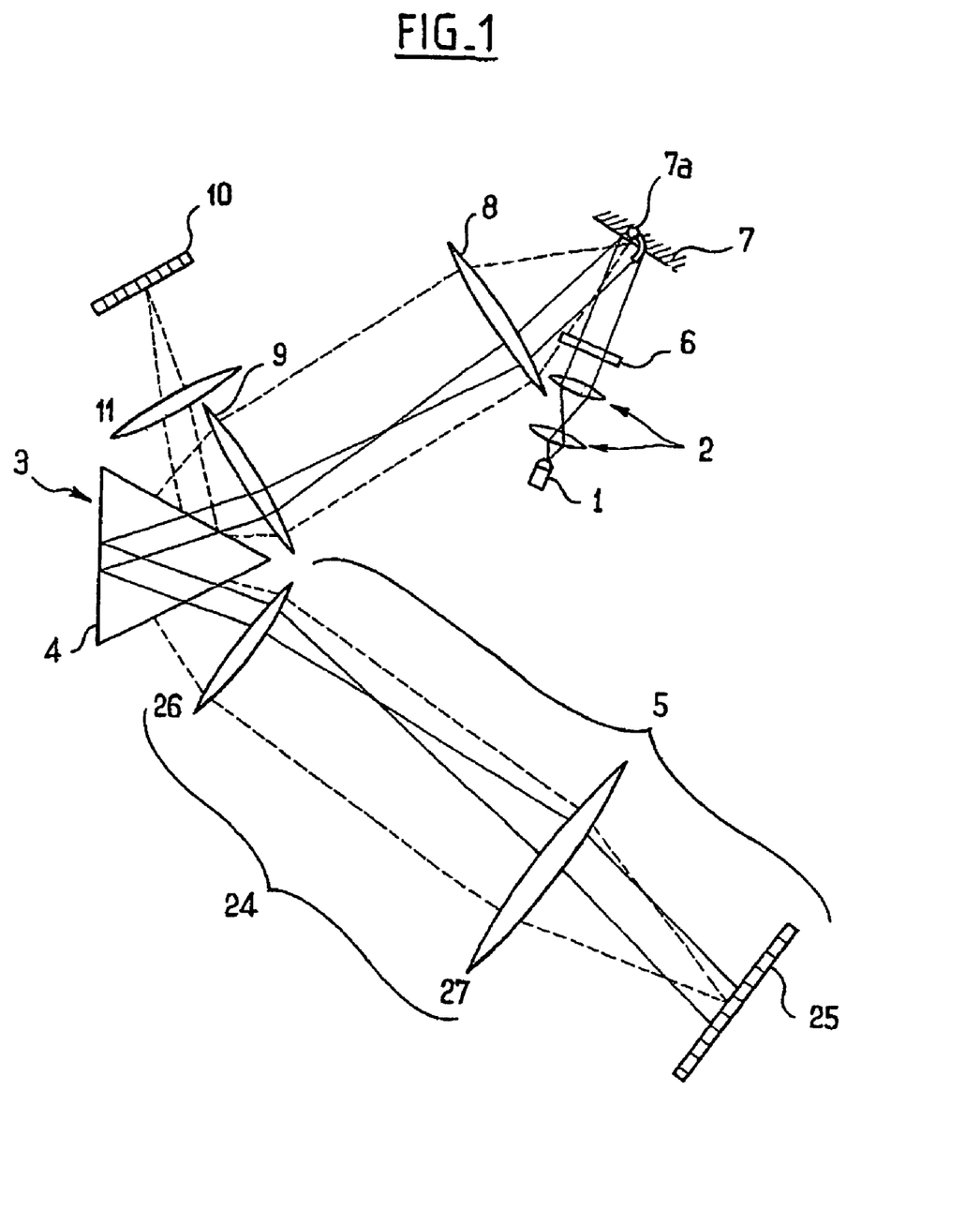
FIG. 1 shows a diagram of the device according to the invention.

The device according to the invention comprises:

a light source 1;

a first collimation system 2 for the incident light beam emitted by the light source;

a reaction cell 3, including at least one prism 4; and an imaging/detection system 5 for the beam reflected by the base of the prism.

The incoherent light source 1 is, for example, a light-emitting diode of narrow spectral width. This maybe, for example, a light-emitting diode of 660 nanometer wavelength and 30 nanometer spectral width.

The beam emitted by the light source 1 is collimated by a collimation system 2. This collimation system 2 is, for example, a system of two microscope objectives for making the light beam parallel.

The light is then polarized by a polarizer 6 so as to be able to excite surface plasmons.

This polarized light illuminates the entrance face of a glass prism 4 of the reaction cell 3.

In one embodiment, the polarized light is reflected by an oscillated galvanometer mirror 7 toward the entrance face of the prism 4, as shown in FIG. 1. The oscillating mirror 7 is made conjugate with the base of the prism by means of two lenses 8 and 9. Thus, the angle of incidence of the beam on the prism may be varied by rotating the oscillating mirror 7 about a spindle 7a perpendicular to the plane of the drawing. The oscillating mirror 7 undergoes a partial rotation, controlled for example by a low-frequency generator.

The rotational movement of the rotation device of the oscillating mirror 7 may be discretized by means of a DC component so as to be able to set the angle at which it is desired to carry out the experiments.

The diameter of the mirror 7 is such that it allows all of the beam incident on the prism 4 to be reflected.

In the embodiment in question, the diameter is at least 10 mm. The total travel of the mirror 7 is 16° for a frequency of 300 megahertz. During its rotation, the oscillating mirror 7 has a continuous fixed-frequency travel.

The lenses 8, 9 used to make the mirror conjugate with the prism 4 may, for example, be lenses of focal length F'=75 mm with a diameter of 35 mm for a 19° excursion or lenses of focal length F'=50 mm with a diameter of 25 mm for a 17° excursion.

FIG. 1 shows in solid lines the limits of the light beam for the position of the mirror 7 shown and in the broken lines the extreme limits of this beam when the mirror 7 occupies the extreme positions of its angular travel.

The angle of incidence of the beam reflected by the mirror 7 on the prism 4 may be determined in various ways.

In a first embodiment, that part of the beam reflected by the entrance face of the prism is collected by an array of CCDs (Charge Coupled Devices) 10 of sufficient length.

This coupled CCD array 10 is used to detect the incidence of the beam.

The beam thus reflected by the entrance face of the prism is focused onto the CCD strip 10 by means of a lens 11 whose focal length is chosen so as to use the entire area of the array 10.

For a CCD array 10 of length L=12.7 mm composed of 512 pixels, it is possible to use a lens 11 of focal length F'=48 mm and diameter 30 mm, for example.

In another embodiment (not shown), the oscillating mirror 7 is rotated by a mirror for determining the position of incidence for each position of the mirror. For example, a variable stepper motor may be used.

Figure 2:
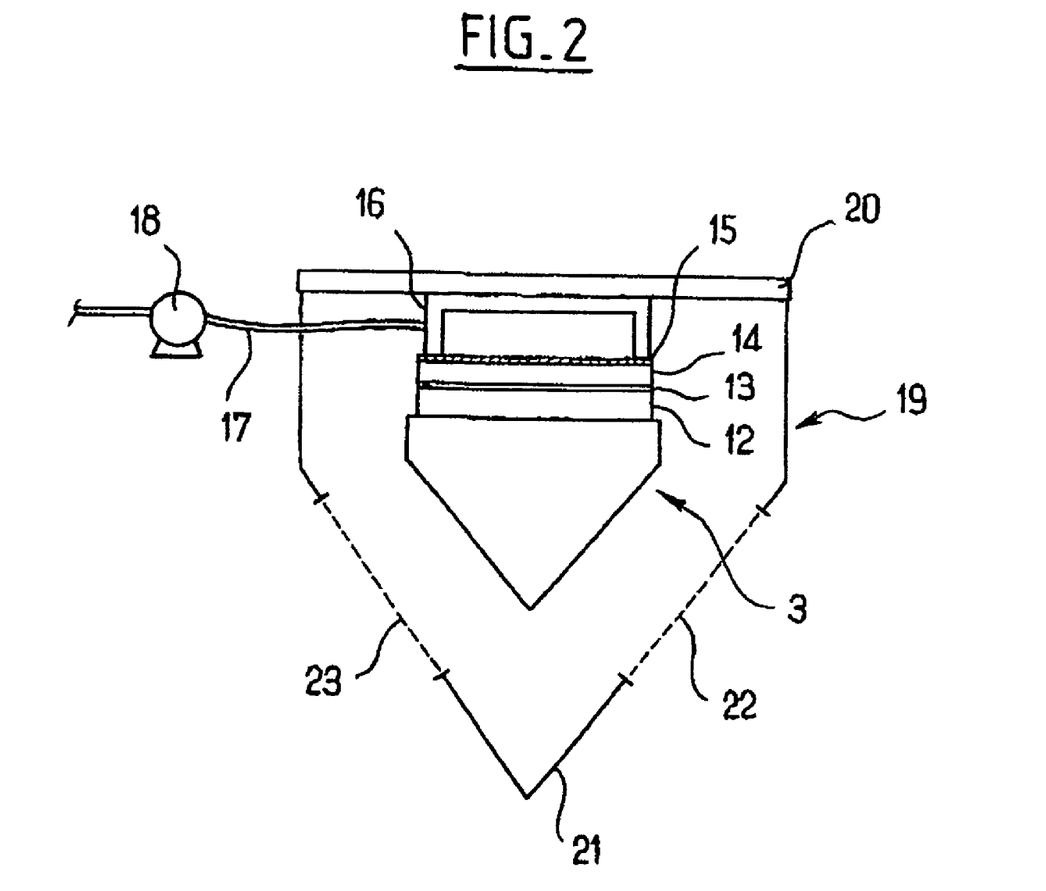
FIG. 2 shows a diagram of the reaction cell according to the invention.

The reaction cell 3 includes at least one glass prism 4, the geometry and the index of which are such that the intermediate image of the object plane in the prism 4 is virtually parallel to the detection plane of the imaging/detection system 5.

In one embodiment, the prism is made of glass of 1.8 index and is characterized by an apex angle of 40° and a base 10 mm in width and 25 mm in height. The distance between the two parallel faces of the prism is 8 mm.

A glass plate of 12 having the same index as the prism 4 is fixed to the base of the prism via an index-matching oil.

A thin chromium film 13, a thin gold film 14 and a film 15 to be characterized are deposited in succession on this glass plate 12.

The chromium film 13 is used to ensure adhesion of the gold film 14 to the glass plate 12 in the presence of an aqueous medium. The thickness of the thin chromium layer 13 is, for example, between 1.5 and 2 nanometers.

The thickness of the thin gold layer 14 is, for example, between 40 and 50 nanometers and preferably around 45 nanometers.

For an application involving a qualitative and quantitative measure of molecular interactions, the film to be characterized is, for example, an organic film 15.

The organic film 15 may be deposited in the form of a continuous film or in the form of spots, as indicated above. In the case of a continuous film, containing only one kind of ligand (for example, an antibody), it is appropriate to deposit solutions of analytes (for example peptides when searching for minotopes) at discrete points in the form of spots, and then a rinsing operation is carried out in order to remove the analytes not specifically fixed.

In the case of an organic film in the form of spots, the sensitive film may be brought into contact with a fluid containing an analyte to be studied.

The ligands are immobilized on the gold film in a known manner.

For example, for studying interactions between oligo-nucleotides and single-strand DNA fragments to be studied, the organic film 15 used for fixing oligo-nucleotides to the gold film 14 by means is a polymer, such as for example polypyrrole, the oligonucleotides being grafted onto the polypyrrole. This polymer has the advantage of being very stable, allowing the organic film 15 comprising the probes (immobilized oligonucleotides) to be reused several times. The production of such a grafted polypyrrole film and its deposition on a gold film are, for example, described in patents EP 0 691 978 and FR 2 789 401.

Once the glass plate 12 has been fixed to the base of the prism 4, it is hermetically sealed by a pan 16.

This pan 16 is, for example, made of PTFE and allows solutions of analytes to be introduced by means of one or more lines 17. A peristaltic pump 18 of variable output may then be used to make these solutions flow.

In order to optimize the introduction of the solutions, the peristaltic pump 18 meets the following criteria:
  it is remotely controllable;
  it can generate outputs of between a few microliters per minute and a few hundred microliters per minute (around 300 to 400 ml/min); and
  it allows an input/output control of the speed of rotation at the start and at the end of injection. The entire reaction cell 3 (prism 4 and pan 16) may be enclosed in an adiabatic chamber 19 shown in FIG. 2, so as to control and maintain the temperature of the system and of the products injected.

The temperature will, for example, be maintained at 37° C. so as to allow any type of biological molecule to be detected.

The adiabatic chamber 19 preferably has an opening (not shown) allowing easy access to the detection cell 3.

The chamber may have in particular a heating baseplate 20, such as for example a copper resistance element, to which the PTFE reaction pan 16 will be fixed. This baseplate 20 is covered by a cover 21 enclosing the entire detection cell 3.

Side windows 22, 23 are provided in the cover 21 so as to let through the light beams on either side of the prism. For example, they are made of glass or any other material allowing the light beams to pass without disturbing them.

A coil (not shown) wound around the line 17 of the pan 16 allows the injected products to be maintained at the temperature of the cell.

An imaging/detection system 5 is placed on the same side as the exit face of the prism 4 so as to receive the reflected beam via the base of the latter.

This system comprises an afocal conjugation/magnification system 24 and a CCD camera 25.

The afocal magnification system 24 is used here to magnify the image of the useful zone of the gold film 14 on the entire CCD camera 25.

The useful zone of the gold film 14 is, for example, around 25 mm² approximately.

In the embodiment shown, a magnification M=1.6 is produced and a system of NA (Numerical Aperture)=1.6 is used to make the image conjugate with the plane of the CCD camera 25.

The afocal system 24 may, for example, comprise a lens 26 of focal length F'=50 mm and of 35 mm diameter, and then another lens 27 of focal length F'=80 mm and of 40 mm diameter.

The lens 26 is placed in such a way that the image of the useful part of the active film after refraction on the exit face of the prism lies in the object focal plane of 26. As a result, the image forms in the image focal plane of the lens 27.

The conjugation system may also be formed, for example, by a first lens of 80 mm focal length and 31.5 mm diameter and a second lens of 65 mm focal length and 25 mm diameter (the combination having an aperture of 2.6). To design this optical system, commercially available optical calculation software, such as CODE V (Optical Research Associates) may be used.

The CCD camera 25 (or simply a CCD matrix) may, for example, have a sensitive area of 6.4 mm×5.8 mm, composed of 768×576 pixels.

The CCD detector may also be, for example, an offset-head camera of 1.5 inch format, with a sensitive area of 6.4×4.8 mm$^2$, comprising 751×582 active pixels, with a signal sampled over 8 bits, or else a compact camera of ⅔ inch format, having a sensitive area of 8.57×6.86 mm$^2$, comprising 1280×1024 active pixels with a signal sampled over 12 bits. These cameras are commercially available.

All the elements of the device according to the invention are controlled automatically by means of a computer system (not shown).

The method of using said device comprises the following steps:
- angular scan of the surface of the glass plate 12 covered with the gold film 14 and the film 15 to be characterized;
- determination of the angle of incidence for which the sensitivity of the imaging/detection system 5 is a maximum for the entire plate 12;
- positioning of the oscillating mirror 7 in order to obtain this angle of incidence; and
- measurement of the reflectivity by the imaging/detection system 5 over time.

The device is then used to characterize the surface of the active zones of the film 15 that are to be characterized.

The device may be applied to the study of molecular interactions.

To measure the interactions between the organic film 15 and analytes, the step of measuring the reflectivity is carried out simultaneously with the introduction into the reaction cell 3 of analytes (unlabelled), the interactions of which with the ligands of the organic film 15 are to be analyzed.

Thus, the change in the interactions between the organic film 15 and the analytes introduced are measured.

These measurements may be carried out under nonselective conditions, so that all the interactions may occur and be studied.

The imaging/detection system 5 allows the optical thickness—the geometrical thickness multiplied by the refractive index of the medium—at any point in the useful part of the gold film 14.

It is thus possible for the zones of equal optical thickness to be topologically displayed and the surface to be characterized.

Thus, during the angular scan of the surface of the glass plate 12 covered with the gold film 14, the system 5 allows the geometrical thickness of each point in the film 14 to be determined and therefore the surface state of the latter to be verified.

The contrast measured during the scan is also used as a reference level for the real-time measurement.

During the real-time measurement, the imaging/detection system 5 measures the variation in the reflectivity with respect to the reference level recorded during the angular scan.

This measurement of the variation in the reflectivity is carried out at any point in the useful part of the gold film 14.

Since the reflectivity varies with the molecular species present on the surface, this measurement allows qualitative analysis by determining the various interactions between the organic film 15, the gold film 14 and the molecules introduced.

Thus, when one is at the angle optimizing the sensitivity of the device, a positive variation in the reflectivity indicates the presence of analytes interacting with the ligands of the organic film 15, a zero variation indicating the absence of an interacting analyte.

However, a negative variation therefore shows a loss of material, that is to say a degradation of the film 15.

By measuring the amplitude of the variation in the reflectivity in real time, it is inherently possible to determine the number of molecules of analytes per unit area and therefore the concentration at each point (in each spot) of the gold film 14 of the analyte molecules introduced.

The device according to the invention therefore also allows quantitative analysis of the molecules that have interacted with the ligands of the film 15.

Depending on the force bonding the film 15 to the gold film 14 and on the nature of the interactions studied, it will be possible at the end of the measurement to regenerate the organic film 15, removing all the analyte molecules that have reacted with it.

It is therefore possible to reuse the film 15 for studying interactions with other analyte molecules.

To optimize the sensitivity of the measurement, the distribution of the spots fixed to the film 15 may also be optimized. This is because it is necessary for the number of probes (ligands) per spot to be high enough to be distinguished from the background noise of the measured signal, without accordingly the probes being too close to one another since a large number of probes entails considerable steric hindrance and impedes the interaction of molecules with adjacent probes. When studying interactions between oligonucleotides and single-strand DNA fragments to be studied, the method according to the invention has many advantages. The interactions are studied under nonselective hybridization conditions, for example at a temperature of around 37° C., so that all the interactions between the reactants can be observed simultaneously.

The device makes it possible to monitor, in real time and without markers, several hundred molecular interactions at a time. In particular, it is capable of discriminating the presence of a point mutation within a DNA fragment.

The discrimination technique relies on the fact that the molecular association may either be total, if the DNA sequence is strictly complementary with that of the oligonucleotide, or partial, if the DNA sequence possesses a mutated base.

The thermodynamics applied to DNA show that, for a fixed location in the sequence, the optical thickness varies according to the type of mutation. It follows that the device can determine the type of mutation precisely.

Under nonselective conditions, if a normal sequence and the three sequences carrying the mutation of one of the bases of said sequence, that is to say the four sequences of which one of the bases has been mutated, are deposited in the form of four different spots on the gold film 14, the device can measure a different signal for each of the immobilized sequences.

In fact, whatever the sequence of the fragment to be analyzed, the device measures a total interaction and three partial interactions.

Depending on the immobilized sequences, it is then sufficient to refer to existing tables giving the force of interaction between bases in order to determine the exact nature of the DNA sequence.

Consequently, if the detection system is calibrated, for example with respect to the value of a completely complementary signal, it is no longer necessary to immobilize the normal sequence and the three mutated sequences—it is sufficient to immobilize only a single sequence.

The capacity of addressing DNA sequences on a solid substrate is therefore increased by a factor of four.

Since the device according to the invention monitors the molecular interactions directly and in real time, it is unnecessary to carry out the measurement at a temperature favoring a single interaction, as in the case of methods using fluorescent markers.

This is because such methods make it possible to record only a single interaction visible at a given temperature. If these methods were to be employed at room temperature, all the markers would emit fluorescence at the same time and could therefore not be differentiated.

The following examples illustrate the invention.

EXAMPLES OF PRISM CONFIGURATIONS

1) Data for a glass of index n=1.776:
    material: SF11 (supplier: SCHOTT);
    optimum apex angle: 30.6°;
    anamorphosis coefficient: 0.479;
    ratio of aberration size to image size: 4.17%.
2) Data for a glass of index n=2.20:
    material: lithium niobate $LiNbO_3$ (supplier: CRYSTAL TECHNOLOGY Inc., Palo Alto, Calif.);
    optimum apex angle: 77.4°;
    anamorphosis coefficient: 0.7;
    ratio of aberration size to image size: 1.57%.
3) Data for a glass of index n=3.33:
    material: GaAs (supplier: AXT Inc., Palo Alto, Calif.);
    optimum apex angle: 123.7°;
    anamorphosis coefficient: 0.89;
    ratio of aberration size to image size: 0.5%.

The design of the prisms was carried out using the MATLAB software (from the company Math Works), making it possible to establish appropriate algorithms using known methods. For a given index n, there is at least one apex angle allowing the intermediate image of the base of the prism through the exit face to be perpendicular to the optical axis of the second afocal conjugation system. Next, a search is made, in the same way, for the pairs (index/apex angle) that give a minimum angular deflection for this intermediate image.

The prisms may also be made using single crystals, such as lithium tantalate ($LiTaO_3$) or lithium niobate ($LiNbO_3$) single crystals.

These are birefringent materials, that is to say they can have a different index depending on the polarization state of the light. This drawback may be overcome for example by orienting the axes of the crystal so that the effective refractive index, in magnetic transverse polarization, is the same whatever the angle of incidence of the beam on the useful zone.

Another solution is to use semiconductor materials such as gallium arsenide, germanium (index of around 4) or silicon (index of about 3.9).

All these materials exhibit good transmission in the infrared, this being favorable on account of the useful characteristics of surface plasmons at high wavelengths.

APPLICATION EXAMPLES

1) Discrimination of Point Mutations

A sensitive zone provided with four 25-base long DNA sequences—a normal or native sequence (WT) of the K-ras gene, a test sequence (CP) used as negative control and two mutated sequences M1 and M5 that differ from the native sequence only by a single base on the same codon—was used.

It is known that mutations of the K-ras gene almost invariably generate a cancer, hence the need to identify individuals possessing a mutation.

These four sequences were immobilized covalently, in the form of four spots, by an electrochemical process described in patent applications WO 94/22889 and WO 00/47317.

The first step consisted in studying the reflectivity of the sensitive zone as a function of the external angle of incidence in order to determine the angle for observing hybridizations with a maximum sensitivity. Next, the CP complementary sequence, in a hybridization buffer at 22° C. (BPS: 137 mM NaCl), was injected so as to demonstrate that only the CP spot reacted, which was the case. Since the experiment had guaranteed by the previous step that the system was selective, after having regenerated the system with a 50 mM sodium hydroxide solution, the next step was to inject the WT complementary sequence, this reacting very well with the WT spot, little with the two spots corresponding to the mutated sequences and not at all with the CP spot. Then, after regeneration, the M1 complementary sequence was injected, this reacting very well with the M1 spot, little with WT and M5 and not at all with CP. The last injection gave the expected results, namely the M5 complementary sequence reacted very well with M5, little with WT and M1 and not with CP.

It is possible to measure the affinities for each of these hybridizations and assert that, depending on the number of molecules that have interacted on the native or mutated spots and depending on the affinity value, it is possible in this way to discriminate a point mutation and even to identify the type of mutation.

After having established the standard reflectivity curves as a function of time, for the four types of hybridization, it is possible to detect, by comparison, a point mutation with only two probes, as indicated in the description.

2) Analysis of Protein-Protein Interactions

A sensitive zone provided with four spots, three of which carry antibodies, was used. Two antibodies were directed against hCG—human pregnancy hormone—which, when it is detected in a man is very often indicative of a testicular cancer. The third antibody was an anti-rabbit antibody, which does not crossreact with human.

It was simply absorbed on a polymer spot. The last spot contained only polymer, without any antibody.

Firstly, bovine serum albumin, which limits the passive adsorption of nonspecifically recognized molecules, was injected until saturation. Next, hCG in a PBS buffer was injected. Since the spot carrying only polymer exhibited no interaction behavior (no change in the reflectivity over time) and the spot carrying the anti-rabbit antibody exhibited interaction behavior that decreased over time, this meant that the antibodies, weakly attached to the polymers, were desorbed and removed from the reaction pan. The other two spots each exhibited interaction behavior of exponential form, indicative of hCG recognition by the antibodies. However, since the two anti-hCG antibodies were different, a difference in the slope at the origin of the interaction behavior curves was noted. This is because their affinity for hCG was not the same. For one of the antibodies, it was deduced from the reflectivity results that the affinity was $8 \times 10^{-10}$, i.e. the same value as measured independently by an ELISA technique.

The subject of the invention is also the application of the method described above to the qualitative and quantitative measurement of molecular interactions as described in the present application.

The invention claimed is:

1. An imaging device, comprising:
a light source;
a collimation system to generate a parallel light beam from a beam emitted by the light source;
a polarizer to polarize the parallel light beam into polarized light;
a rotating optical deflector system to reflect the polarized light into a collimated incident light beam;
an optical prism having an apex angle, an entrance face, an exit face and a base provided with a sensitive film, the prism being characterized by its apex angle and by its refractive index;
a first afocal optical conjugation system that:
    is located on a side of the entrance face of the prism;
    has a first optical axis that is fixed with respect to the prism and is oriented so that after the collimated incident light beam has passed through the first afocal optical conjugation system, the collimated incident light beam is directed toward the entrance face, is refracted, then strikes the base of the prism where it undergoes total reflection and emerges, after refraction, on the exit face, forming a reflected emergent beam; and
    has an orientation and an aperture that are such that the collimated incident light beam refracted on the entrance face illuminates all of at least what is called a useful part of the sensitive film, and undergoes thereon a total reflection when a direction of the collimated incident light beam exiting the first afocal optical conjugation system varies, on either side of the first optical axis, over an angular range of at least 10° in total, the useful part containing active zones whose optical thickness is likely to vary over time;
a second afocal optical conjugation system that is placed on a side of the exit face of the prism, the second afocal optical conjugation system having a second optical axis, fixed with respect to the prism that is oriented so that, when the collimated incident light beam is parallel to the first optical axis, a second emergent beam parallel to the second optical axis exits the second afocal optical conjugation system;
a detection system having a plane sensitive surface that is capable of receiving and analyzing the second emergent beam, the plane sensitive surface being perpendicular to the second optical axis;
wherein:
    the second afocal optical conjugation system has an aperture such that any light emanating from the useful part passes through the aperture when the direction of the collimated incident light beam varies over the angular range;
    the second afocal optical conjugation system is configured such that any light emanating from the useful part illuminates the sensitive surface of the detection system; and
    the apex angle and the index of the prism are configured such that, when the direction of the collimated incident light beam is parallel to the optical axis of the first afocal optical conjugation system an intermediate image of the useful part that has passed through the exit face of the prism and that constitutes an object for the second afocal optical conjugation system, is perpendicular to the second optical axis.

2. The device as claimed in claim 1, wherein:
the second afocal optical conjugation system has a depth of field; and
the apex angle and the index of the prism are configured such that, when the direction of the collimated incident light beam varies over the angular range, an angular deflection of the intermediate image of the useful part formed through the exit face does not exceed the limits of the depth of field.

3. The device as claimed in claim 1, wherein the angular range is at least 12° or at least 14° or at least 16°.

4. The device as claimed in claim 1, wherein a magnification of the second afocal optical conjugation system is configured such that the part of the emergent beam exiting the second afocal optical conjugation system and emanating from the useful part illuminates an entirety of the sensitive surface of the detection system.

5. The device as claimed in claim 1, wherein:
the second afocal optical conjugation system comprises a first dioptric system, and a second dioptric system;
wherein:
    the emergent light beam exiting the second afocal optical conjugation system successively passes through the first dioptric system and the second dioptric system, and then is sent to the sensitive surface of the detection system; and
    the intermediate image exiting the exit face of the prism is in the object plane of the first dioptric system.

6. The device as claimed in claim 1, wherein the optical deflector system comprises a rotating plane mirror capable of pivoting about an axis parallel to one edge of the prism.

7. The device as claimed in claim 1, wherein the detection device is capable of analyzing the emergent beam exiting the second afocal optical conjugation system so as to measure and/or compare a reflectivity of any point zone of the useful part.

8. The device as claimed in claim 1, wherein the detection device comprises a CCD or CMOS matrix.

9. The device as claimed in claim 1, wherein the sensitive film has, in the active zones, at least one population of immobilized ligands.

10. The device as claimed in claim 1, wherein all optical elements are fixed with respect to one another except for the optical deflector system.

11. The device as claimed in claim 1, wherein the optical deflector system comprises only a single rotating mirror.

* * * * *